(12) United States Patent
Horvath

(10) Patent No.: US 9,931,237 B2
(45) Date of Patent: Apr. 3, 2018

(54) PORTABLE RESETTING DEVICE

(76) Inventor: Peter Horvath, Longmeadow, MA (US)

( * ) Notice: Subject to any disclaimer, the term of this patent is extended or adjusted under 35 U.S.C. 154(b) by 2157 days.

(21) Appl. No.: 12/586,224

(22) Filed: Sep. 18, 2009

(65) Prior Publication Data

US 2010/0106067 A1    Apr. 29, 2010

Related U.S. Application Data

(63) Continuation-in-part of application No. PCT/US2008/003516, filed on Mar. 18, 2008, and a continuation-in-part of application No. 12/309,366, filed on Jan. 15, 2009, now abandoned.

(30) Foreign Application Priority Data

Mar. 20, 2007    (HU) .................................... 07 00228

(51) Int. Cl.
     *A61F 5/00*      (2006.01)
     *A61F 5/04*      (2006.01)
     *A61H 1/02*      (2006.01)

(52) U.S. Cl.
     CPC ............. *A61F 5/04* (2013.01); *A61H 1/0281* (2013.01)

(58) Field of Classification Search
     CPC . A61F 5/04; A61F 5/042; A61F 5/048; A61H 1/0281
     USPC ................. 602/33, 36, 39, 40, 1, 37, 38, 20; 601/33, 24, 26
     See application file for complete search history.

(56) References Cited

U.S. PATENT DOCUMENTS

| 4,616,637 | A | | 10/1986 | Caspari et al. |
| 4,736,736 | A | | 4/1988 | Moers et al. |
| 5,417,643 | A | * | 5/1995 | Taylor ............................. 601/33 |

(Continued)

FOREIGN PATENT DOCUMENTS

| WO | WO 2009/111378 | | 9/2009 |
| WO | WO 2009111378 | A2 * | 9/2009 |

OTHER PUBLICATIONS

"Erfahrungen bei Einrichtung der Schulterverrenkunger" [Experience in Relocating Shoulder Dislocations]. Der Chirurg. 1941, vol. 13, p. 4162.

(Continued)

*Primary Examiner* — Victoria J Hicks
(74) *Attorney, Agent, or Firm* — Stan Collier, Esq.

(57) ABSTRACT

The portable resetting device (100) has a portable pedestal (126) with telescoping sections (172/170). An underarm support (102) of adjustable height is mounted to a lower support (114) that is mounted to the pedestal (126). A traction structure (112) for transmitting forces to an injured arm is mounted to the lower support (114). A computer controllable motor (124) is operatively connected between the lower support (114) and the pedestal (108) so that an angle of tilt (116) may be placed thereon. An arm-holding plate (136) is attached to the lower support (114) and moves in a longitudinal direction by means of another computer controllable motor (118) operatively connected therebetween. An auxiliary arm support (122) is operatively connected by a computer controllable motor (120) on the lower support (114) and provides an additional force to the humerus head. A computer (302) controls the resetting device (100) and may communicate to a support computer (210) for treatment advice.

15 Claims, 10 Drawing Sheets

(56) References Cited

U.S. PATENT DOCUMENTS

| | | | | |
|---|---|---|---|---|
| 5,919,148 A | * | 7/1999 | Marko et al. | 600/595 |
| 5,997,494 A | | 12/1999 | Watkins et al. | |
| 6,644,322 B2 | * | 11/2003 | Webb | 128/899 |
| 2004/0049143 A1 | * | 3/2004 | Short | 602/33 |
| 2005/0251076 A1 | | 11/2005 | Branch | |

OTHER PUBLICATIONS

"Repositionalsstuhl" [reposition chair], manufacture: Dr. Franz Merska, Vienna, Austria.
International Search Report and Opinion, dated Jul. 25, 2008, PCT/US08/03516.
International Search Report and Opinion, dated Sep. 14, 2010, PCT/US10/01459.
"Erfahrungen bei Einrichtung der Schulterverrenkunger" [Expereinces in Relocating Shoulder Dislocations], Der Chirurg. 1941, vol. 13, p. 4162.
"Repositionsstuhl" [reposition chair], Manufacture: Dr. Franz Merska, Vienna, Austria.

* cited by examiner

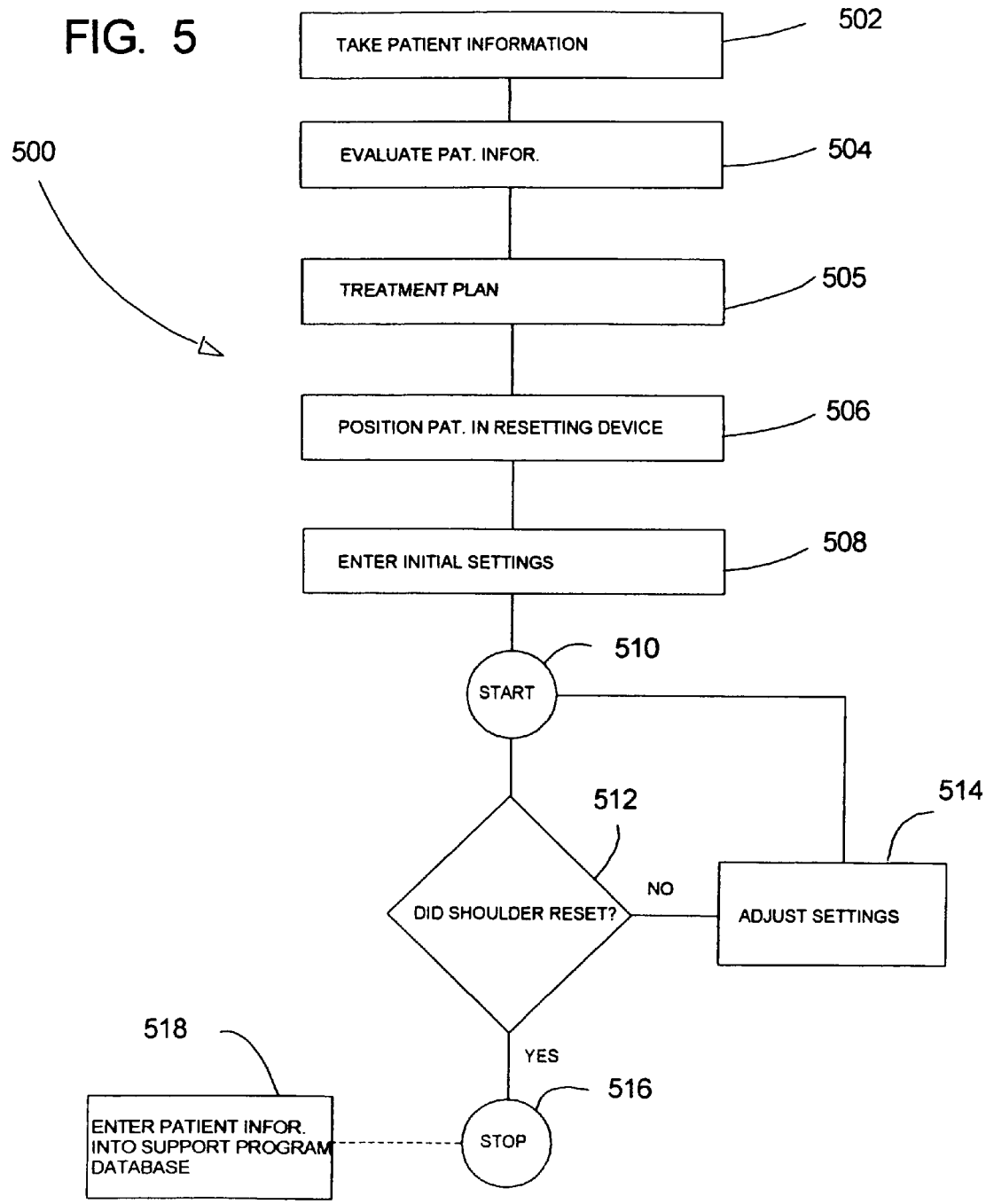

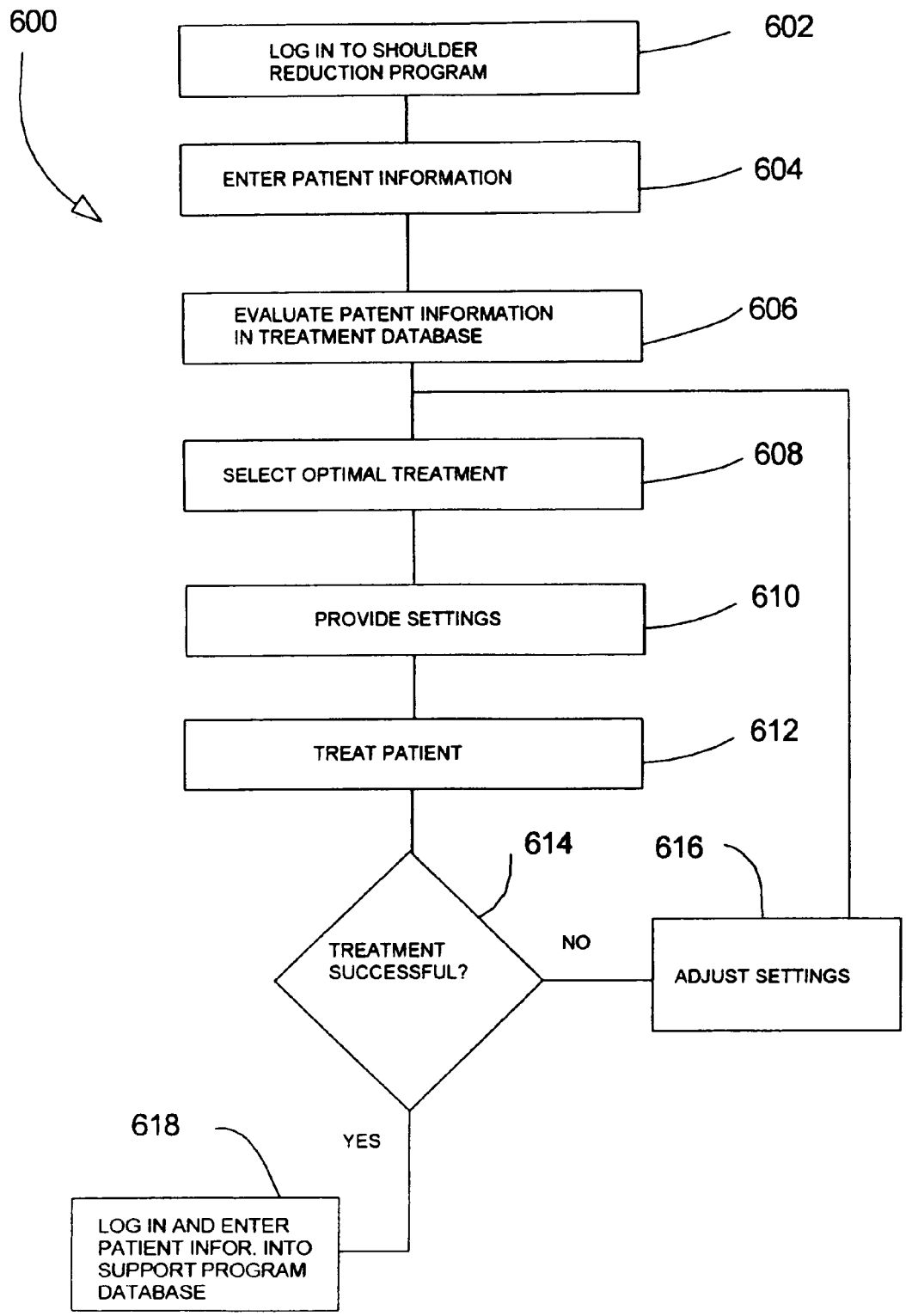

PORTABLE RESETTING DEVICE

CROSS REFERENCE TO RELATED APPLICATIONS

The present patent application is a continuation-in-part to International Patent Application PCT/US2008/003516 filed on 18 Mar. 2008, and is a continuation-in-part to and claims priority to Hungarian Patent Application Serial Number P 07 00228 filed on 20 Mar. 2007, and is a continuation-in-part to U.S. patent application Ser. No. 12/309,366 filed Jan. 15, 2009 by the same inventor.

REFERENCE TO FEDERALLY SPONSORED RESEARCH OR DEVELOPMENT

NA

REFERENCE TO JOINT RESEARCH AGREEMENTS

NA

REFERENCE TO SEQUENCE LISTING

NA

BACKGROUND OF THE INVENTION

Field of the Invention

The present invention relates generally to medical systems for use in the treatment of injuries, and, in particular, relates to a device for treating joint injuries, and, in great particularity, relates to a device for resetting a joint dislocation, and in greater particularity, relates to an electromechanical means for controlling the treatment to minimize pain and the use of anesthesia.

Description of the Prior Art

With people being more active in sports today such as soccer, football, basketball, hockey, etc., more and more people are receiving shoulder injuries, and in particular, dislocations of the shoulder wherein the humerus head of the arm is pulled away from the tablet of the fossa glenoidalis joint surface. This is a painful injury.

Resetting of the shoulder is primarily addressed by peculiar manipulations or pulling of the upper arm in various directions as has been done in the past. It is a well known fact that moving the dislocated joint is painful so most methods are not even attempted without administering pain reduction drugs. In the pulling method, the pulling is typically done by human strength—in various directions—or with a weight, acting mostly downward according to the law of gravity.

An example of the latter method for relocating shoulder dislocations is the so-called Stimson technique, during which the injured arm of the patient, who is lying on his/her abdomen, is pulled down perpendicular to the body with the use of weights. This method is disclosed in U.S. Pat. No. 5,997,494, according to which a quantity of fixed weights depending on the patient's physical condition and the state of the dislocation (advantageously with a mass of 4.5-12 kg) is placed in a weight container connected to a cuff attached to the lower arm of the patient. Alternatively, water may be added to a container in an increasing amount; in this manner, a smooth extension can be achieved.

Another prior art example for treating the shoulder dislocation is disclosed in U.S. Pat. No. 4,616,637, according to which the arm of the injured person, who is lying on his/her side, is pulled upward by attaching to the hand a rope passing through an overhead pulley.

The essence of the above examples is thus that the limb of the injured person is pulled with weights thereby extending the muscles whose contraction must be overcome during the relocation of the dislocation. Their disadvantage is the length of the traction pull and the solutions used to exert force can cause pain because of possible displacements of the arm; therefore drugs (sedatives, local anesthesia, muscle relaxants) are generally needed. Administering drugs, however, can always be associated with side effects, including serious complications.

Only a few methods may work without drug administration. One of these is the Arlt method, where the relocation always takes place without giving drugs! (Arlt: "Erfahrungen bei Einrichtung der Schulterverrenkungen" [Experiences in Relocating Shoulder Dislocations], *Der Chirurg*. 1941, vol. 13, page 416 2). This method has been practiced in a sparing manner and mostly painless. Its essence is that for every dislocation, there is one position that is "practically" pain free. This is generally the position where the patient holds the dislocated arm with the good arm.

Sometimes, however, the task of the physician is to find this pain-free position by fine movements of the shoulder. Maintaining this position, the patient is made to sit so that his shoulder girdle is supported in the underarm by a back support of a chair, then, while maintaining this position, the arm is pulled downward in a sparing manner and gradually until the dislocated humerus head jumps back into the glenoid cavity. A chair having this adjustable underarm support has been specifically designed for this procedure: (manufacturer: Dr. Franz Merska, Vienna, Austria, product name: "REPOSITIONSSTUHL" [REPOSITION CHAIR]").

The above methods may present one or more disadvantages to the patient. For example, the position of the arm changes during pulling by manual force thus causing pain. It also has the disadvantage that the extent and strength of the pulling force cannot be measured exactly in relation to the extension of the arm; one of the main reasons for failure, however, is that the physician gets tired and gives up.

Accordingly, there is an established need for a device that prevents the above mentioned uncertainties and can be applied in a controlled manner without the use of drugs for resetting a dislocated shoulder.

SUMMARY OF THE INVENTION

The present invention is thus achieved by a portable resetting device that overcomes the above disadvantages and provides a device that assures painless reduction of the shoulder dislocation.

The device of the present invention is directed at a goal of providing a pain-free position while relocating the humerus head into the tablet. The device of the present invention for reduction of a shoulder dislocation provides a portable resetting device having an underarm support of adjustable height upon a pedestal with the resetting device being located near to a chair having the patient therein and the injured arm on the same side as the resetting device. The resetting device is portable and thus may be readily moved to the patient. A traction structure suitable for transmitting a mechanical force in a downward direction to the injured arm is mounted to a lower support that is further mounted to the top of the pedestal. The traction structure has the lower support/section/part connected to the pedestal. A computer controllable motor is operatively connected between the lower support and the pedestal so that an angle of tilt may be placed thereon. An arm-holding plate that serves to hold the injured arm is attached to the lower support having arm holding supports and/or cuffs attached that keep the arm in a bent and fixed position; the arm-holding plate and the lower support of the traction structure are slideably connected to each other so as to permit them to move in the longitudinal direction with respect to each other by means of another computer controllable motor operatively connected therebetween. An auxiliary arm support is operatively connected by a controllable motor on the lower support. The pedestal includes the controllable motors for moving the lower support in angular displacement and for adjustment in the height of the underarm support. Appropriate electronic circuits are provided to control the motors, to display device information, and to remotely control the motors. The resetting device may further be connected through a network or the Internet to a central office where patient treatment information may be placed in a database and a treatment plan provided.

The resetting device may be a stand-alone device, or may communicate to a support program over the Internet for assistance and advice in the treatment of patients.

Therefore, one aspect of the present invention is a traction structure adjustable through an angle of about 20 to about 50 degrees with respect to a vertical plane, and even more advantageously between 30 and 40 degrees;

It is another aspect of the present invention to provide a means for measuring the force of extension of the joint so that the physician can control the application of force to the shoulder in an accurate manner;

It is yet another aspect of the present invention to provide, in addition to the underarm support, an auxiliary arm support placed in a position more distant from the body for moving the humerus head further away from the body as needed;

It is still a further aspect of the present invention to provide stabilization of the bent arm by one or more supports; one of which is placed nearer the elbow on the side opposite to the direction of the pulling force and the other placed on the side nearer the wrist, in the direction of the pulling; and It is still a further aspect of the present invention to provide for the resetting device being portable and controllable to better suit the conditions of the patient.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which:

FIG. 5 is a flow diagram for operating the resetting device of the present invention; and FIG. 6 is a flow chart for a reduction program;

Like reference numerals refer to like parts throughout the several views of the drawings.

DETAILED DESCRIPTION OF THE PREFERRED EMBODIMENTS

The present invention is directed at a resetting device for reduction of a shoulder dislocation that minimizes pain, and further eliminates or greatly reduces the need for any pain drugs for the procedure.

Figure 1A:
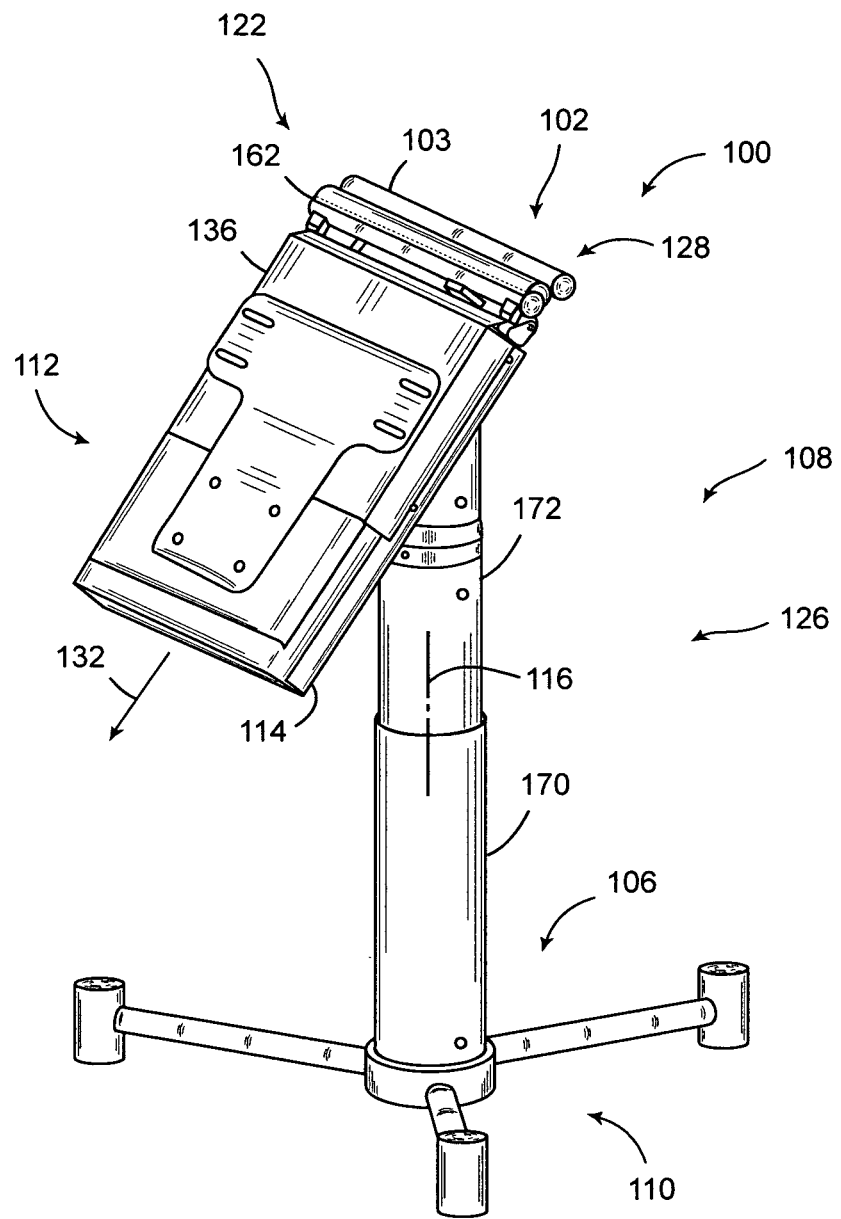
FIG. 1A is a front-side perspective view of a resetting device of the present invention.

Turning to the drawings, wherein like components are designated by like reference numerals throughout the various figures, attention is initially directed to FIGS. 1A to 1F which illustrate a resetting device 100, and, in particular, FIG. 1A which is a front-side perspective view of an embodiment of the resetting device 100.

In FIG. 1A, a right side injured shoulder, for example, not shown, is supported by an underarm support 102 having an underarm support member 103. A patient, not shown, is sitting in a chair, not shown, facing the front with the right arm, not shown, over the underarm support member 103 with the armpit resting against the underarm support member 103. The height of the underarm support 102 can be adjusted by a computer controlled motor 104, FIG. 1C, located in a base 106 of a pedestal 108 of the resetting device 100. It should be understood that the controlled motors driving a screw may be otherwise accomplished in that function. Forces, distances and angles may be visibly measured by scales attached to the appropriate devices. Pneumatic or hydraulic or mechanical drive systems may be adapted to similarly function as would be understood by one skilled in the art knowing of the present invention as disclosed herein. The pedestal 108 has a lower section 170 and an upper section 172 that telescopes out of the lower section 170. The control motor 104 drives a screw 105 that is rotatably attached to an end plate 109 located in the upper section 172. The base 106 has a triangular set of feet 110. A traction structure 112 is adjustably attached to a lower support 114. Attached to the upper part of the lower support 114 is an auxiliary arm support 122 having an auxiliary arm support member 162 that is parallel to the underarm support member 103.

Figure 1B:
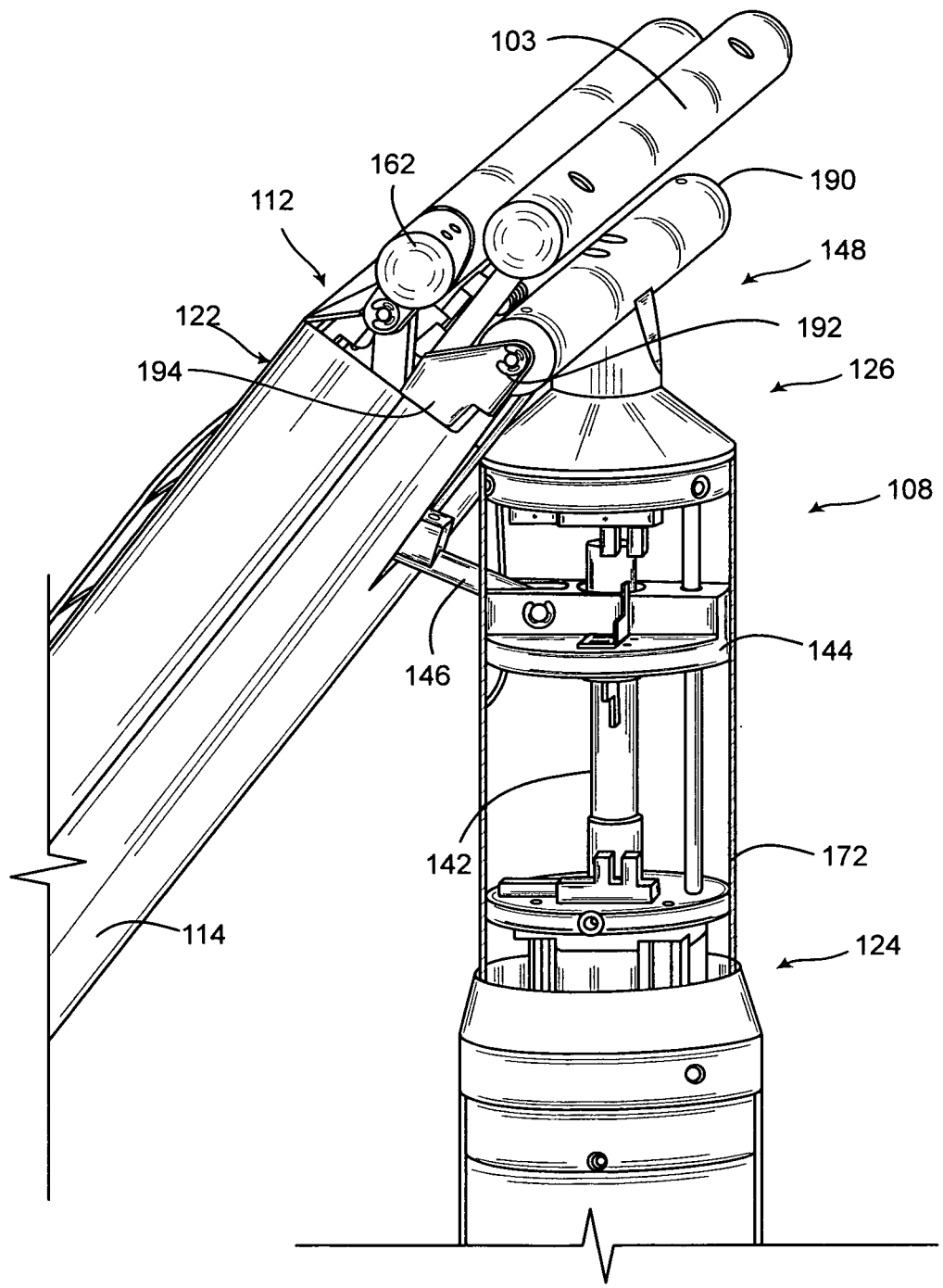
FIG. 1B is an x-ray view of a top of a pedestal of the resetting device.
Figure 1C:
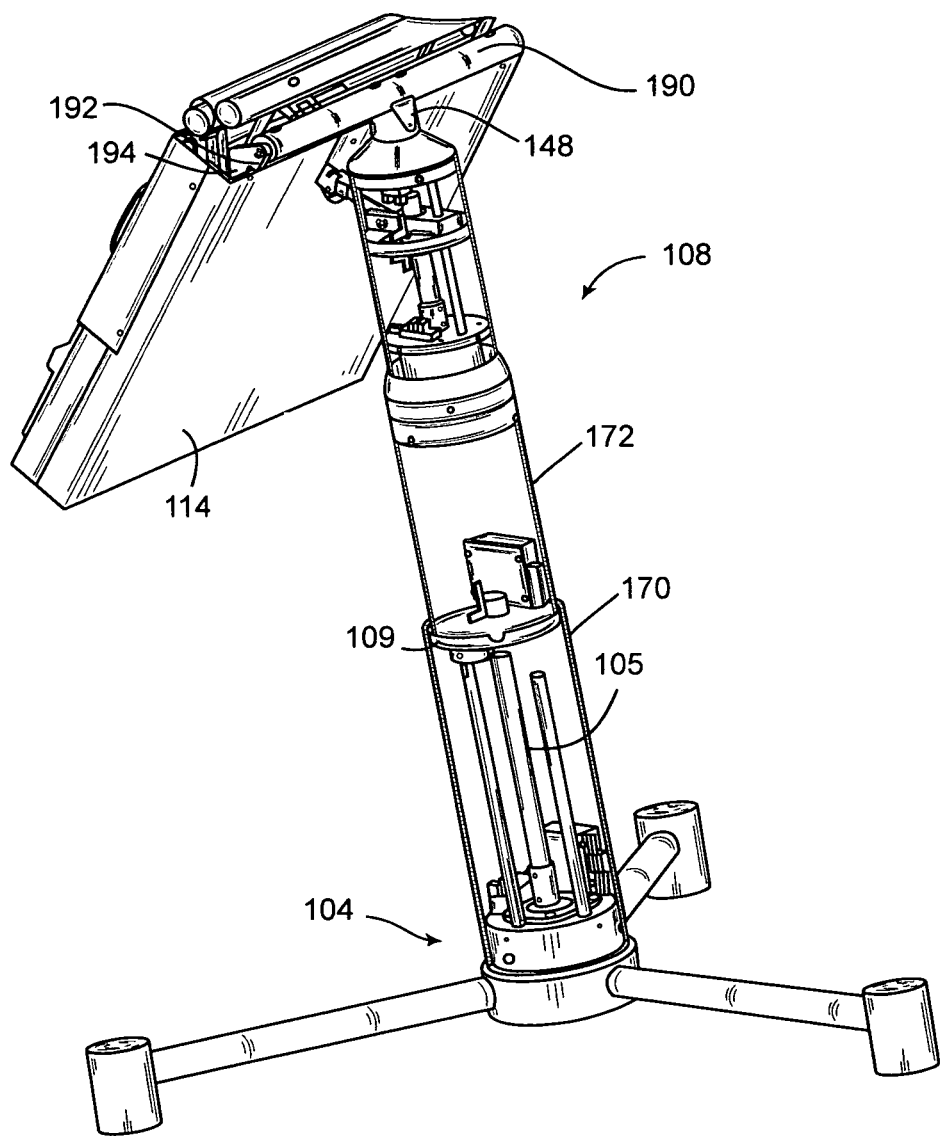
FIG. 1C is an x-ray view of a bottom of the pedestal of FIGS. 1A and 1B

As seen in FIG. 1B, the traction structure 112 is adjustably attached to the pedestal 108 at a top mount 148. An arm-holding plate 136 is translatably mounted to the lower support 114 and moves along a pair of slides 140, FIG. 1D. A tilt angle α, FIG. 1A, between the traction structure 112 and a vertical axis 116 of the pedestal 108 is adjustable through a tilt angle computer controlled motor 124 mounted in the upper section 172 of the pedestal 108, FIG. 1B. The motor 124 turns a screw 142 that translates a platform 144 therein. Pivotally mounted to the platform 144 is an arm 146 that is further mounted pivotally to the backside of the lower support 114. As the platform 144 is raised, the arm 146 pushes up the lower support 114 which is further pivotally mounted to the top mount 148. The translation of the platform 144 causes the lower support 144 to pivot off of the top mount 148.

Figure 1D:
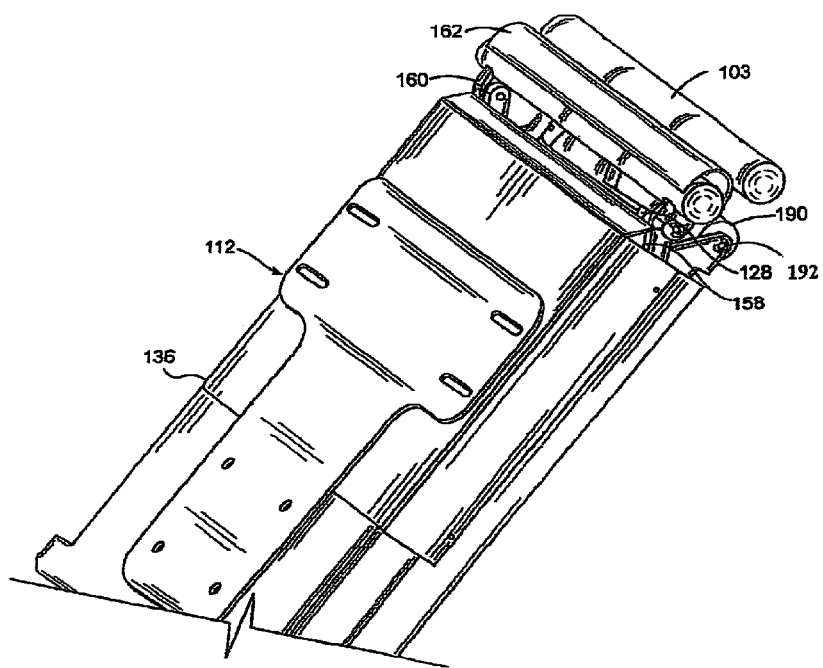
FIG. 1D is a partial perspective view of a traction structure with the arm-holding plate partially deployed.
Figure 1E:
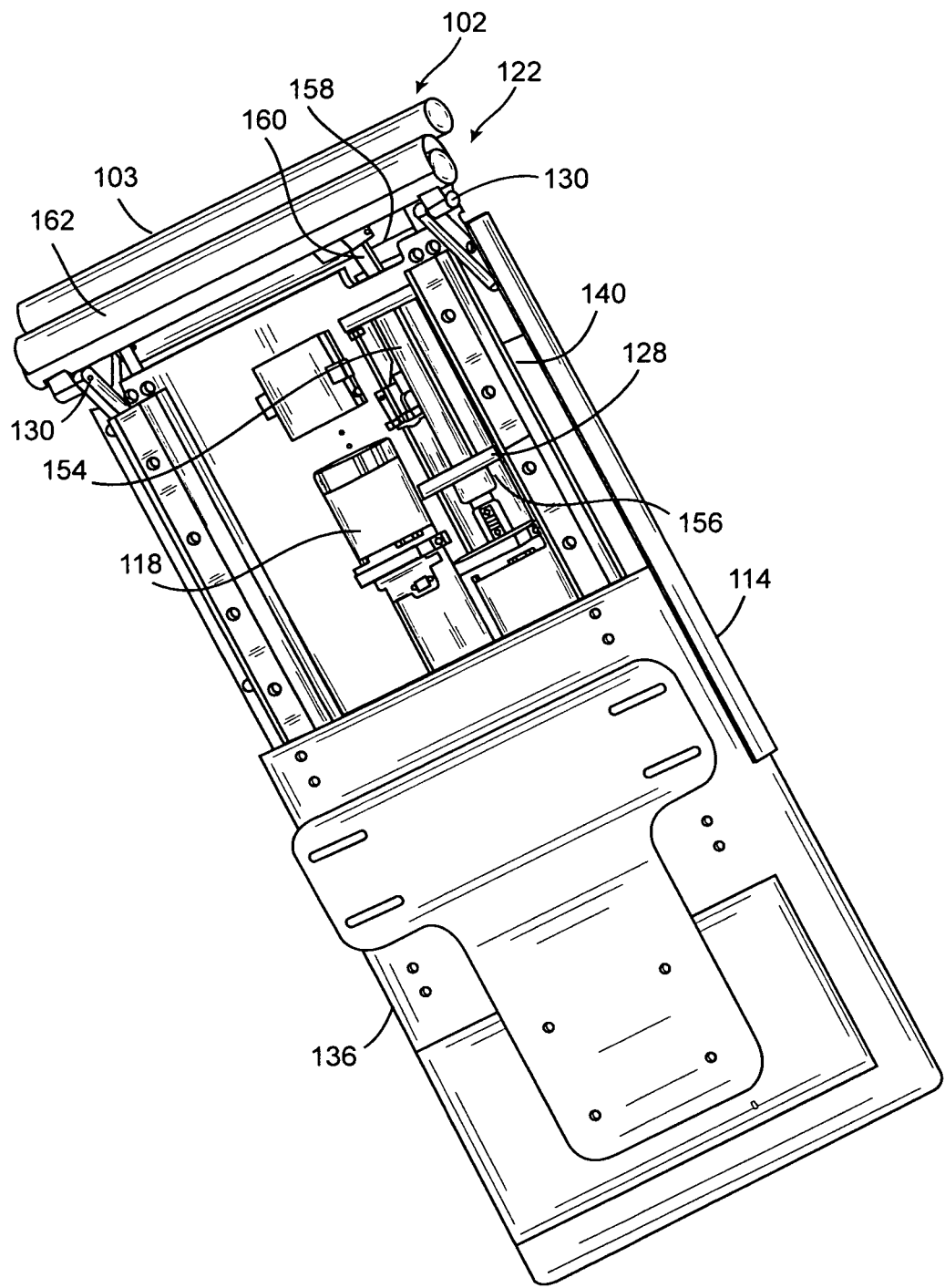
FIG. 1E is a partial view of an underarm support and auxiliary arm support.

The movement of the arm-holding plate 136, FIGS. 1A, 1D and 1E, is adjustable through a force providing computer controlled motor 118 that is also adjustable. The motor 118 is mounted in the lower support 114 and drives a screw 150, FIG. 1F, that has a translatable bracket 152 mounted thereto that is further mounted to a backside of the arm-holding plate 136.

Figure 1F:
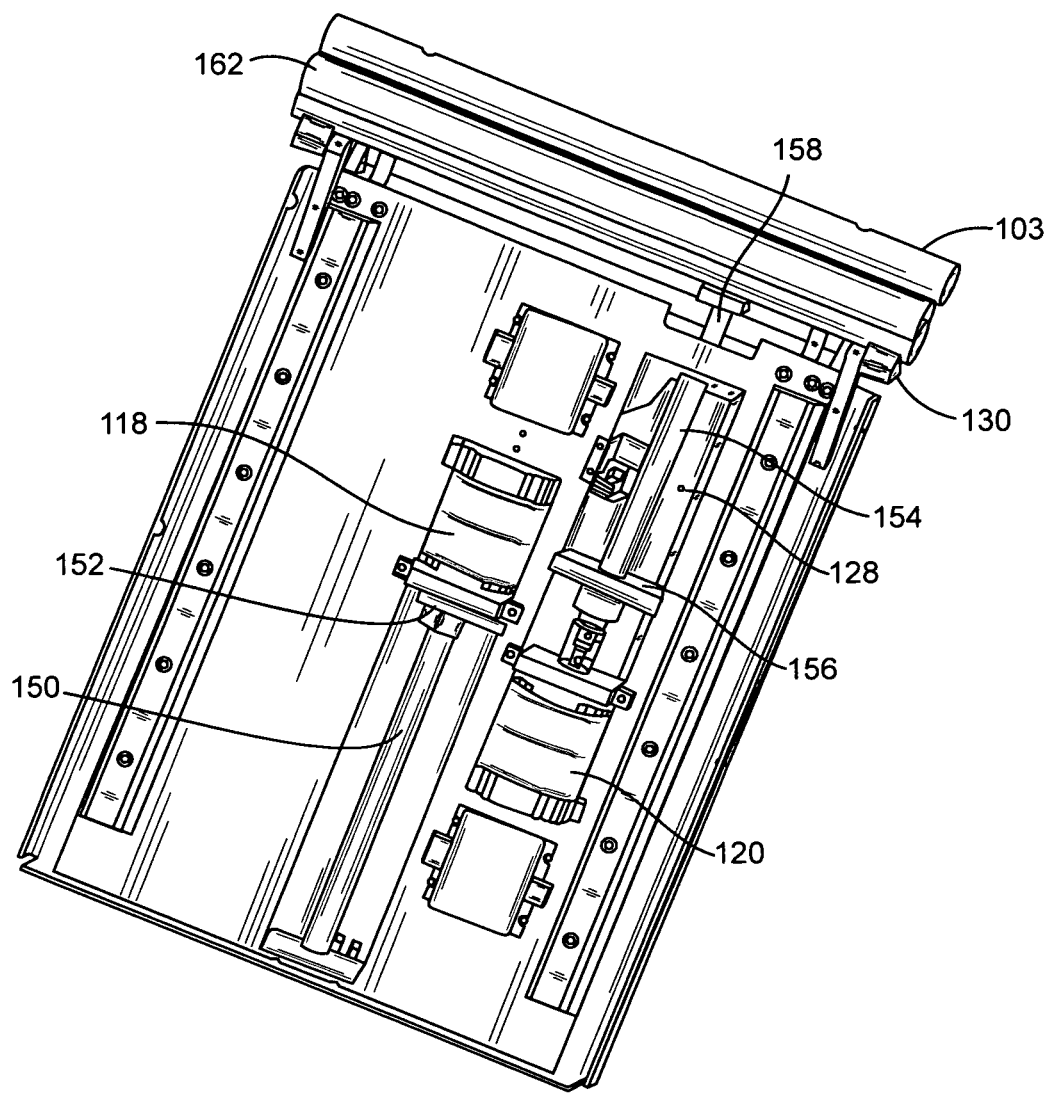
FIG. 1F is a top view of a lower support of the traction structure.

A further feature of the resetting device 100 is an auxiliary arm support 122, FIGS. 1A, 1D, 1E, and 1F, that may be moved to a distal location parallel to the underarm support member 103. An auxiliary arm support computer controlled motor 120, FIG. 1F, is located in the lower support 114 of the traction structure 112 and is adjustable and drives linkage 128 that causes the auxiliary arm support member 162 to rotate about a pivot 130. As seen in FIG. 1D, the motor 120, not shown, drives a screw 154 that has a translatable bracket 156 thereon. The bracket 156 has a lower arm 158 pivotally attached thereto and is further pivotally connected to an upper arm 160 that is connected to the auxiliary arm support member 162. As the bracket 156 is moved up, for example, the lower arm 158 pushes the upper arm 160 up also and causes the member 162 to move away from the parallel underarm support member 103 by rotating on the pivot 130.

The role of the auxiliary arm support 122 becomes important if the traction force on the stabilized arm in the pulling direction, as shown by an arrow 132, FIG. 1, is insufficient by itself to reset the dislocated shoulder. In this case, repositioning is achieved by actuating the motor 120 that acts through linkage 128 to move the auxiliary arm support member 162 away from the body by means of the pivot 130; thus exerting an additional outward pressure on the upper arm.

In carrying out the method of the present invention, the patient is made to sit in a chair adjacent to the resetting device 100. The underarm support member 103 is placed below the injured shoulder with the aid of the height adjustment motor 104 lifting the underarm support member 103 upwards into the armpit. Movement of the patient's injured shoulder should be minimized and thus the underarm support lowered initially to clear the armpit. Because of variations in patient's height and size, the chair may be lowered or raised also. The angle $\alpha$ of the traction structure 112 is set and fixed corresponding to a pain-free position as determined by the treating doctor. The traction structure 112 is able to rotate over an angle $\alpha$, wherein the angle $\alpha$ ranges from about 20 to 50 degrees with respect to a vertical plane, and more effectively in a range between about 30 to about 40 degrees. The lower arm of the patient is stabilized in a bent position with the aid of the supports attached to the arm-holding plate 136. The patient may be secured in the chair to prevent undesired movements that may result during the treatment.

The following is an example, and only provides a general description of the manner of applying the force to the shoulder dislocation. The traction force, in direction 132, is initially set to start at 50 N (MKS system, Newton). The traction force is set with the aid of a remote controller 400 as shown in FIG. 4. The remote controller 400 may communicate to a computing device 302, FIG. 3, by hardwire or by RF or by IR sensor 402. Further, the information presented and actions needed may also be taken and shown on a display of the computing device 302. The power to the resetting device 100 is turned on by pressing a power button 408 that may be illuminated green when actuated. A power shut off button 404 or kill switch is used to immediately stop the procedure and return the resetting device 100 to its initial or default settings. A start/stop button 410 is used to stop the treatment temporarily so that adjusts can be made and then restarted. The initial settings or adjust settings are entered via a set 412 of switches that control the motors on the resetting device 100. Normally the switches are off unless either an up button 414 or down button 416 are actuated. Buttons 414 and 416 are for controlling the height of the underarm support 102 by adjusting the height of the pedestal 108. Optionally related information may be shown in a remote controller display 418. For example, an angle switch 420 when either actuated up 422 or down 424 will then display the actual angle in degrees. An auxiliary arm support switch 426 having an up 428 and a down 430 switch will then display the angle in the display 418. A force button 432 with an up 434 and a down 436 buttons when actuated will then display the force in metric Newtons or English pounds. As the up or down button is held, the appropriate motor will adjust the device in a controlled manner, from the last setting, not to cause any alarm or pain in the patient. For example, the force button 432 may be tapped to cause the force to come up to the desired level. A light within the button may flash when this adjustment is being made. This is within the control of the treating doctor based upon the conditions of the patient. The traction is started by pushing the start button 410. At this time, the force motor will start to increase the force on the arm-holding plate in a downward direction. The traction is continued for about 1 minute, then the traction force is increased in steps of 25 N at further 1-minute intervals (to a maximum of 200 N). The extension may be further observed with the aid of a scale attached between the arm-holding plate 136 and the lower support 114 of the traction structure 112. If repositioning does not occur, then the auxiliary arm support 122 is moved away from the body as desired. As this is done, an additional force appears in the outward direction, perpendicular to the axis of the extended position of the joint.

FIG. 5 illustrates by flow chart the steps required in the treatment of a patient using the resetting device 100 of the present invention. Patent information is taken in step 502 which would include sex, age, weight, height, present medication, nature of the injury, whether it has happened before, prior treating doctors, hospitals, medications given, etc. This information is then evaluated in step 504 which may also include x-rays, MRIs, physical examinations, etc. A treatment plan is then proposed in step 505. The patient is then positioned in the resetting device 100 in step 506. Initial settings are entered into the computing devices associated with the device 100 in step 508. The treatment is initiated by pressing the start button in step 510. If this initial treatment is not effective in resetting the shoulder, the settings are adjusted in step 514 and the treatment is again continued and evaluated.

Figure 2:
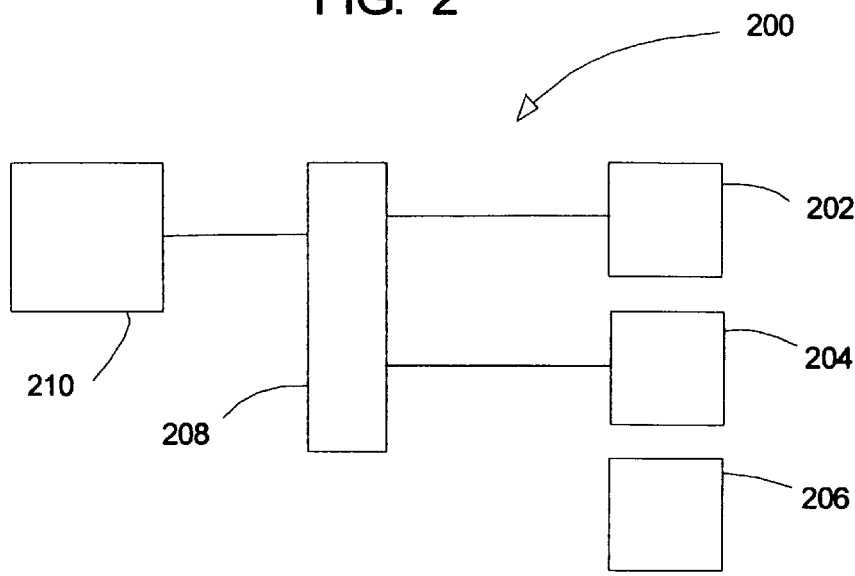
FIG. 2 is a diagram showing the resetting device communicating to a support program.

FIG. 2 indicates a plurality of resetting device 202, 204, 206, et. seq., that communicate through a network, such as the Internet 208, to one or more shoulder reduction centers 210 that operate one or more programs 600, FIG. 6, for managing the resetting devices in a shoulder reduction system 200. It should be understood that the system 200 may be a Windows® based program owned by Microsoft. The treating doctor after logging into the system 200, step 602, would enter the patient's information, step 604, such as noted above. The system 200 would then evaluation the patient information in light of a treatment database in step 606. Based upon this information, optimal treatment settings in step 608 such as height of the arm support 102, the angle of the arm holding plate α116, the extension of the arm holding plate 112 with an initial force, and if needed the angle of the auxiliary arm support 122, are provide in step 610. The resetting device would upload patient information and this would be evaluated based upon past histories maintained in one or more databases in the centers 210 to recommend possible treatment plans. If the treatment is successful in step 614, and the shoulder is reset, step 516, the treatment history is entered into the support program database in step 518, and step 618. If the initial settings did not reset the shoulder, adjusted settings would be provided in step 616 through the program 600. This information would be clearly labeled advisory in nature and subject to the actual conditions of the patient as seen by the treating doctor.

Figure 3:
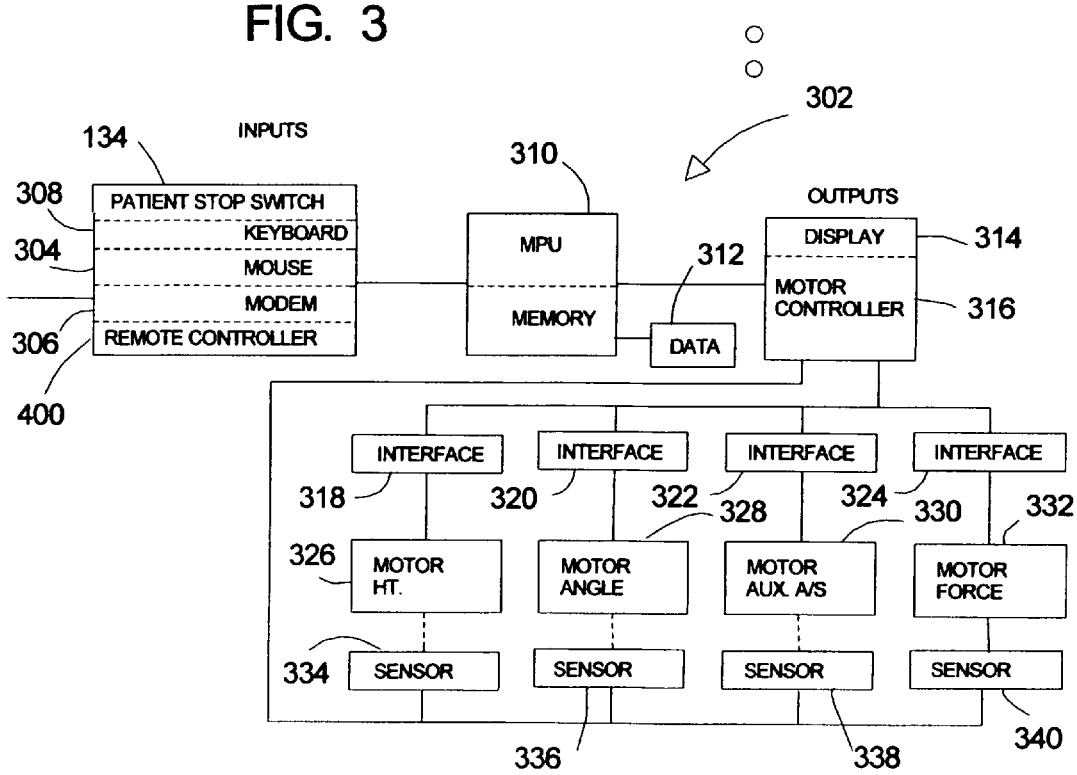
FIG. 3 is an electrical block diagram for the resetting device of the present invention.
Figure 4:
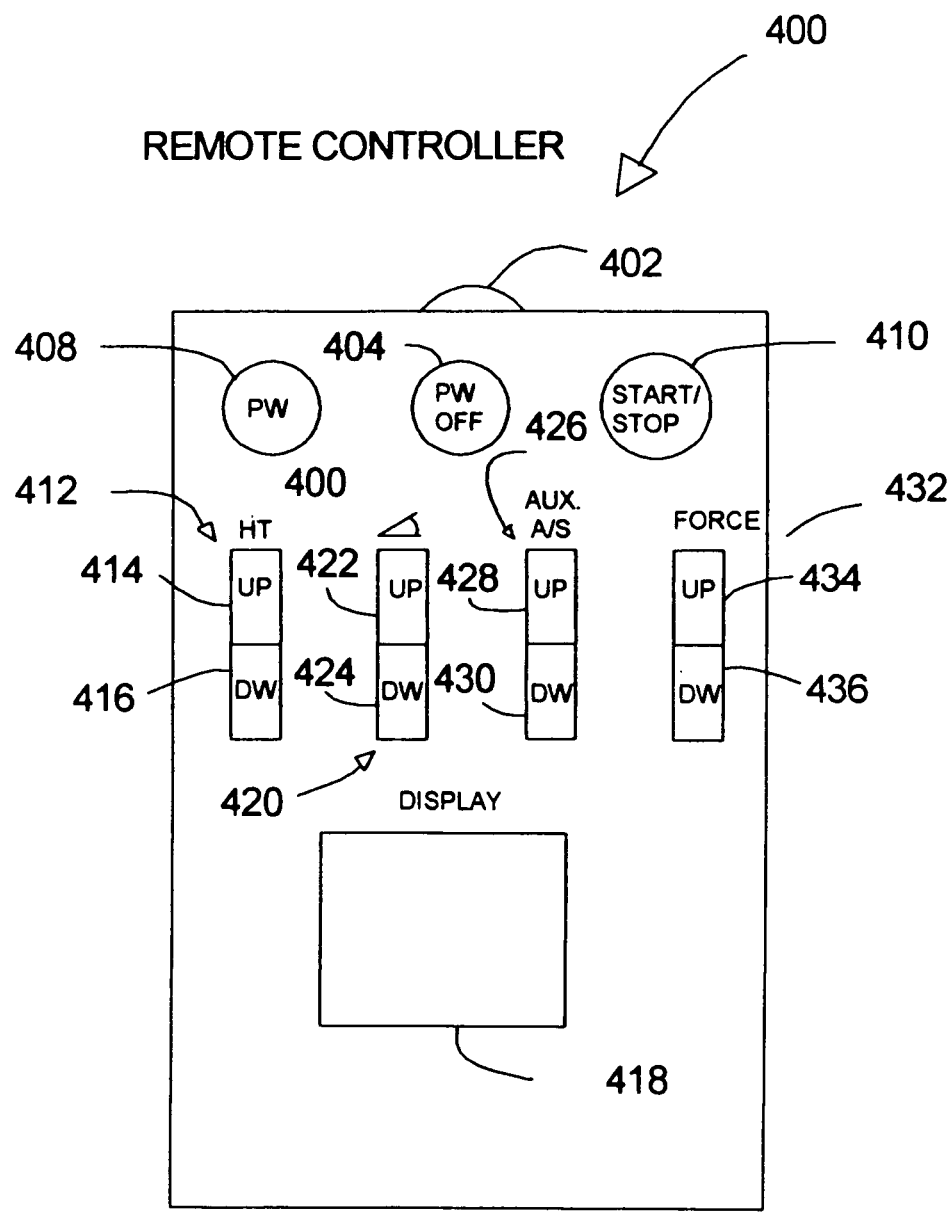
FIG. 4 is a front view of a remote controller for operating the resetting device of the present invention.

FIG. 3 illustrates the computing device 302 for operating the resetting device 100. The computing device 302 may also include additional computers such as laptop computers that are interfaced thereto to display and control information. Inputs into the computing device 302 include but are not limited to the remote controller 400, a patient "kill" switch 134, and other traditional devices such as a mouse 304, a modem 306 connected to a network and/or the Internet, a keyboard 308, a touch screen display, etc. The patient "kill" switch 134 may also be provided that allows the patient to terminate the treatment cycle if the pain is excessive. These operate through a conventional microprocessor unit 310 having a data storage unit 312 that would be running a dedicated program for supporting the resetting device 100. Outputs would include displays 314 and, in particular, a motor controller 316. The motor controller 316 would operate through interfaces 318, 320, 322, and 324, to control adjustable height motor 326, angle adjustment motor 328, auxiliary arm support adjustment motor 330, and force adjustment motor 332. The operations of these motors would be monitored by sensors 334, 336, 338, and 340 that would communicate this information back to the processor 310 and the motor controller 316.

For example, if there is no resistance to moving the arm-holding plate, the current through the force adjustment motor 332 will be a fixed value, but if there is resistance, i.e., the arm is being pulled, the current will increase and this corresponds to a force applied. The motor controller 316 will note this increased current by an increase in voltage across a resistor in that circuit, for example. This voltage will correspond to a particular applied force determined empirically and stored in a table in the data storage unit 312 of the computing device. The adjustable height motor 326, the angle adjustment motor 328, and auxiliary arm support adjustment motor 330 may be controlled based upon the run-time. For example, the angle adjustment motor 328 run-time would correspond to an angle of the arm-holding plate/traction structure in another table, run-time versus angle, stored in the computing means. Similarly to both the adjustable height motor 326 and the auxiliary arm support adjustment motor 330 where the run-time would correspond to distance. This information thus can be digitized and displayed and further changed based upon inputs from the remote controller 400.

It should be understood that all electrical wiring to the electric motors and control wires and other electronic devices are considered conventional and would be known to one skill in the art with knowledge of the present invention and as illustrated in FIG. 3.

With the system and method of the present invention, a pain-free relocation of the shoulder joint can be achieved, during which, the physician only has to pay attention to directing and checking the process and the patient. During the process, the amount of extension and the direction can be monitored and kept under control. Further, data is produced, previously unknown, which can be very important in treating dislocations in the future. The following important features of the present invention are thus provided: 1) To support the shoulder by measuring the desired height; 2) To set the basic pain-free position by setting the arm-body angle; 3) To maintain the pain-free position during the entire traction period; 4) To know the traction force at all times, continually, or to make periodic changes to the settings, as desired; 5) To measure the muscle relaxing—arm extension; 6) To direct the pressure on the upper arm outward, which is an important element of certain repositioning techniques.

Since many modifications, variations, and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A portable resetting device (100) for a reduction of a shoulder dislocation adapted for a patient with the shoulder dislocation being seated upon a chair, the portable resetting device (100) comprising:
   an underarm support (102), said underarm support (102) being adjustable in height;
   a traction structure (112) for transmitting mechanical forces to an injured arm of the shoulder dislocation, said traction structure (112) having an arm-holding plate (136) translatably mounted thereto; a lower support (114) having the arm-holding plate (136) thereon, and the underarm support (102) mounted thereon; and
   an auxiliary arm support adjustably mounted to said lower support (114).

2. The portable resetting device (100) as recited in claim 1, further including a display for indicating an angle of the traction structure (112) to a vertical plane and a force applied to the injured arm of the shoulder dislocation by the arm-holding plate (136).

3. The portable resetting device (100) as recited in claim 2, including a computing device (302) for controlling a motor (124, 328) for adjusting the angle of the arm-holding plate (136), and a motor (118, 332) for adjusting a force applied to the injured arm of the shoulder dislocation by the arm-holding plate (136).

4. The portable resetting device (100) as recited in claim 3, further including a controller motor (104, 326) for adjusting a height of the underarm support (102) and a controlled motor (120, 330) for adjusting the auxiliary arm support (122).

5. The portable resetting device (100) as recited in claim 3, further including a remote controller (400) connecting to the computing device (302) for controlling one or more of controlled motors (326, 328, 330, 332) and indicating positions and forces thereon.

6. The portable resetting device (100) as recited in claim 1, including at least one additional support on the arm-holding plate (136) adapted to support the injured arm of the should dislocation in a bent and stabilized position.

7. The portable resetting device (100) as recited in claim 6, wherein the at least one additional support further includes an elbow support adapted for an elbow of the injured arm of the shoulder dislocation and placed in a first direction perpendicular to a traction direction, at least one wrist support placed on a side corresponding to the traction direction (132), the injured arm securable to the arm-holding plate (136).

8. The portable resetting device (100) as recited in claim 1, wherein the auxiliary arm support (122) is in close proximity to the underarm support (102) and adapted to be on an outside position away from a body of the patient.

9. A method for resetting a shoulder dislocation without use of drugs and without pain using a portable resetting device (100), the portable resetting device (100) comprising:
   a traction structure (112) for transmitting mechanical forces to an injured arm of the shoulder dislocation, said traction structure (112) having an arm-holding plate (136) translatably mounted thereto; a lower support (114) having the arm-holding plate (136) thereon and an underarm support (102) mounted thereon; and an auxiliary arm support adjustably mounted to said lower support (114);
   the method comprising the steps of:
   evaluating (502, 504, 505) the shoulder dislocation for treatment;
   positioning (506) a patient having the shoulder dislocation, the patient being seated upon a chair, a shoulder having a dislocation being placed over the underarm support (102) and an auxiliary arm support (122) with the injured arm of the shoulder dislocation removably attached against the arm-holding plate (136);
   adjusting (508) an angle of a traction structure (112)/underarm support (102)/auxiliary arm support (122) to a position minimizing any pain;
   applying a predetermined force in a controlled manner to the traction structure (112) to cause a humerus head of the injured arm of the shoulder dislocation to reset into a tablet; and
   releasing the patient.

10. The method as recited in claim 9, wherein a treating doctor consults with a shoulder reduction center (210) to obtain advice on a treatment plan (505) to optimize and minimize any pain.

11. The method as recited in claim 10, wherein the treating doctor consults with the shoulder reduction center (210) through a computing device (302) connected to a network (200).

12. The method as recited in claim 11, furthering including connecting the computing device (302) to the portable resetting device (100).

13. The method as recited in claim 11, wherein the network (200) is an Internet (208).

14. The method as recited in claim 9, further including a step of re-adjusting (514) a position of the auxiliary arm support (122) to further increase a force applied to the shoulder dislocation, by pressing outward on the humerus head of the injured arm of the shoulder dislocation.

15. The method as recited in claim 9, wherein at least the predetermined force is generated by one or more controlled motors (322, 330, 332).

* * * * *